United States Patent [19]

Pascaloff

[11] Patent Number: 4,641,077
[45] Date of Patent: Feb. 3, 1987

[54] METHOD AND APPARATUS FOR PROVIDING STERILE CHARGED BATTERIES

[75] Inventor: John H. Pascaloff, Goleta, Calif.

[73] Assignee: Hall Surgical-Divison of Zimmer, Inc., Carpinteria, Calif.

[21] Appl. No.: 693,882

[22] Filed: Jan. 23, 1985

[51] Int. Cl.[4] .............................................. H02J 7/00
[52] U.S. Cl. .................................... 320/2; 128/419 PS
[58] Field of Search ...................... 320/2; 128/419 PS; 422/6, 25

[56] References Cited

U.S. PATENT DOCUMENTS 3,939,391 2/1976 Winnacker .............................. 320/2
4,141,367 2/1979 Ferreira ......................... 128/419 PT
4,288,733 9/1981 Bilanceri et al. ......................... 320/2

Primary Examiner—Peter S. Wong
Assistant Examiner—Mark D. Simpson
Attorney, Agent, or Firm—Stuart E. Kreiger

[57] ABSTRACT

A method of providing sterile, charged batteries for use in a sterile field which includes the steps of sterilizing at least one battery and a battery charger, transferring the sterilized battery and charger in a sterile state to the sterile field and charging the battery with the battery charger. The battery charger is adapted to withstand exposure to the environment present during the sterilization process. The sterilizing step may be preceded by an initial charging step in which the battery is charged with a battery charger. A sterilizable battery charger permits implementation of the method.

2 Claims, 1 Drawing Figure

METHOD AND APPARATUS FOR PROVIDING STERILE CHARGED BATTERIES

BACKGROUND OF THE INVENTION

1. Field of the Invention

The present invention relates to methods and apparatus of providing sterile, charged batteries, and, more particularly, to a method of and apparatus for charging such batteries in a sterile field.

2. Description of the Prior Art

A problem associated with the use of battery powered surgical instruments is the difficulty in providing fully charged sterile batteries. The batteries used to power the instruments must be sterilized prior to introduction into the sterile field. If the batteries are charged before being sterilized, they lose about twenty percent of the charge during the sterilization process. If the batteries are charged after being sterilized, the sterility is compromised by exposure to the battery charger. Manufacturers have not heretofore provided sterile chargers because exposing the chargers to the sterilization process damages them. Some manufacturers have offered a disposable drape that can be placed over the charger. The drape includes terminals so that power can be transferred through it.

The aerospace industry has developed a means of sealing the circuits of motors from exposure to the vacuums in which the motor must operate. The motors do not function in a vacuum. Motors used in undersea work have also been sealed to protect them from the detrimental effects of pressure and salt water.

It is an object of the present invention to provide fully charged batteries for use in a sterile field without the risk of contaminating the batteries after they have been sterilized. It is a further object of the present invention to provide a sterile apparatus for charging the sterile batteries in the sterile field.

SUMMARY OF THE INVENTION

The present invention provides a method of and apparatus for providing sterile, charged batteries for use in a sterile field. The method includes the steps of sterilizing at least one battery and a battery charger, transferring the battery and battery charger in a sterile state to the sterile field and charging the battery with the battery charger in the sterile field. The battery and battery charger are adapted to withstand exposure to the environment present during the sterilizing step.

The sterilizing step may be preceded by an initial charging step wherein the battery is charged with the battery charger. The later charging step replaces the charge lost during the sterilizing step.

The battery charger may be hermetically sealed.

BRIEF DESCRIPTION OF THE DRAWING

The single FIGURE is an isometric cutaway view of one embodiment of a sterilizable battery charger used to practice the method of the present invention.

DETAILED DESCRIPTION OF THE PREFERRED EMBODIMENT

Figure 1:
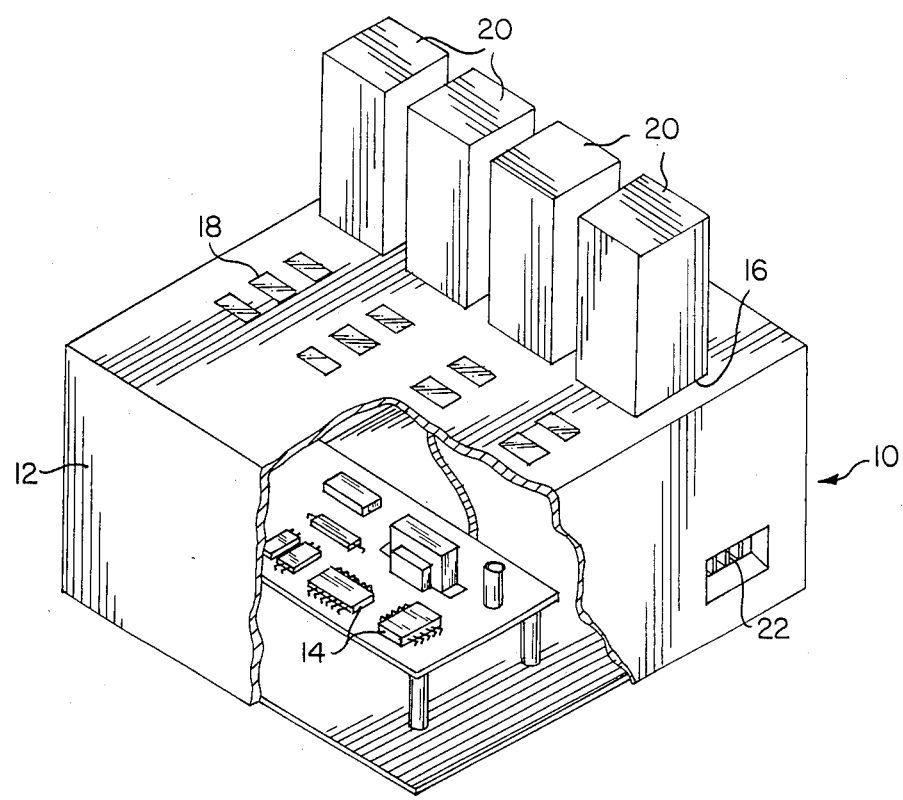

FIG. 1 illustrates an embodiment of a sterilizable battery charger 10 which may be used to practice the method of the present invention. Any suitable charger 10 having components which can withstand exposure to the environment present during a sterilization process can be used. The properties required of the components will vary according to the type of sterilization process employed. Typical processes are steam sterilization, ethylene oxide or hydrogen peroxide sterilization, gamma radiation and glutaraldehyde sterilization.

The battery charger 10 shown in FIG. 1 includes a case 12 housing any electrical circuit 14 suitable for charging batteries. Receptacles 16 on the exterior of case 12 hold batteries 20. Four batteries 20 are shown seated in appropriately sized receptacles 16. Any number of receptacles or other suitable means of operatively connecting the batteries to the charger for the purpose of charging the batteries will suffice.

The battery charger 10 also includes indicators 18, which may be light emitting diodes or any other suitable means to indicate when the charger 10 is operating. A connector 22 for connecting charger 10 to any suitable source of electrical power (not shown) is shown on the exterior of case 12 in FIG. 1.

If the charger 10 is to be sterilized by steam, the case 12 must be made of a noncorrosive, heat tolerant material, such as stainless steel or a gold plated metal. The electronic components of circuit 14 must also be selected for their heat tolerant properties. For example, they should be able to withstand an exposure temperature of about 350° F. The electrical components of circuit 14 are preferably sealed to shield them from the oxidizing environment. Case 12 is hermetically sealed.

The interior of case 12 may be purged of oxygen and filled with nitrogen to eliminate oxidation problems and to minimize the potential for arcing in the event of an electrical failure.

The electrical components of circuit 14 include a transformer. In the preferred embodiment of charger 10, 115 volts AC is delivered through connector 22 to the transformer where it is converted to the appropriate DC charging voltage. The charging voltage is then delivered to the printed circuit and the appropriate voltage is applied to each battery 20.

Sterile, fully charged batteries 20 are provided for use in a sterile field by the following method. At least one sterilizable battery, suitable for the desired end use, and a sterilizable battery charger of the type described above are placed in a sterilizer and sterilized. The batteries and battery charger are made of materials adapted to withstand exposure to the environment present during the sterilization process of choice.

Following sterilization, the battery and battery charger are transferred in a sterile state to the sterile field. To transfer the sterilized items, any suitable airtight container having a sterile interior can be used. A nonsterile person may carry the container holding the sterile battery and battery charger to the sterile field and open the container. A sterile person then may remove the sterile battery and battery charger.

Once in the sterile field, the battery or batteries are inserted in the receptacles on the battery charger. The charger is connected in a sterile manner to a source of electricity by means of the connector or any suitable equivalent means. The batteries are then charged to a desired voltage. The fully charged, sterile batteries are ready for use in a surgical power tool.

In a modification of the above described method, nonsterile batteries may be charged with any suitable nonsterile battery charger prior to the sterilization step. During the sterilization process the batteries lose about twenty percent of the charge. The lost charge can be replaced by charging the sterile batteries with the sterile battery charger in the sterile field.

What is claimed is:

1. A method of providing sterile, charged batteries for use in a sterile field comprising the steps of:

sterilizing at least one battery and a battery charger, said battery and battery charger being adapted to withstand exposure to the environment present during such sterilizing step;

transferring said battery and said battery charger in a sterile state to said sterile field; and charging said battery to a desired voltage with said battery charger in said sterile field.

2. A method as recited in claim 1 wherein said sterilizing step is preceded by an initial charging step wherein said battery is charged with said battery charger.

* * * * *